(12) United States Patent
Silman et al.

(10) Patent No.: US 7,285,123 B2
(45) Date of Patent: Oct. 23, 2007

(54) APPARATUS FOR TREATMENT OF MIDDLE EAR FLUID IN THE EARS OF INFANTS AND TODDLERS

(76) Inventors: Shlomo Silman, 3030 Emmons Ave., Apartment 6R, Brooklyn, NY (US) 11235; Michele Emmer, 1514 E. 31st St., Brooklyn, NY (US) 11234

( * ) Notice: Subject to any disclaimer, the term of this patent is extended or adjusted under 35 U.S.C. 154(b) by 764 days.

(21) Appl. No.: 10/832,532

(22) Filed: Apr. 26, 2004

(65) Prior Publication Data
US 2005/0000520 A1    Jan. 6, 2005

Related U.S. Application Data

(60) Provisional application No. 60/465,401, filed on Apr. 25, 2003.

(51) Int. Cl.
*A61F 11/00* (2006.01)
(52) U.S. Cl. ..................... 606/109
(58) Field of Classification Search ............... 606/108, 606/109, 112, 114, 191, 196, 199
See application file for complete search history.

(56) References Cited

U.S. PATENT DOCUMENTS 4,896,679 A * 1/1990 St. Pierre ............... 128/865

5,885,242 A   3/1999  Arick et al.

OTHER PUBLICATIONS http://www.invotec.net/otovent.html.
Arick, Daniel S. and Silman, Shlomo. "Treatment of otitis media with effusion based on politerization with an automated devices." Ear, Nose & Throat Journal 79 (2000): 290-298.
Silman, Shlomo and Arick, Daniel. "Efficacy of a Modified Politzer Apparatus in Management of Eustachian Tube Dysfunction in Adults." Journal of the American Academy of Audiology 10 (1999): 496-501.
Bluestone, Charles D. and Klein, Jerome O. "Otitis Media in Infants and Children." Philadelphia: W.B. Saunders Company, 1995. 197-200.
Paparella, Michael M. and Shumrick, Daniel A. "Otolaryngology." Philadelphia: W.B. Saunders Company, 1973. 80-82.
Ballenger, John Jacob. "Disease of the Nose, Throat and Ear." Philadelphia: Lea & Febiger, 1969. 634-636.

* cited by examiner

*Primary Examiner*—Kevin T. Truong

(57) ABSTRACT

An apparatus and method is provided for reducing middle ear fluid and equalizing middle ear pressure in infants and toddlers. The apparatus coordinates the act of swallowing and the forcing of air into the nostril of the child. The coordinated actions allow air forced into the nostril to traverse the Eustachian tube when in its open state. A flexible member and a main flexible tube, connected accordingly, are both adapted to be inserted into the child's mouth and nostril, respectively, to achieve such coordination and allow air to enter the Eustachian tube when in its open state, ultimately allowing air to reach the middle ear.

5 Claims, 7 Drawing Sheets

APPARATUS FOR TREATMENT OF MIDDLE EAR FLUID IN THE EARS OF INFANTS AND TODDLERS

CROSS REFERENCE TO RELATED APPLICATION

This application claims the benefit of provisional Patent Application No. 60/465,401, filed Apr. 25, 2003, which is hereby incorporated by reference herein in its entirety.

BACKGROUND OF THE INVENTION

1. Field of the Invention

The present invention relates to an apparatus and method for the equalization of middle ear pressure. More specifically, the present invention relates to an apparatus and method for preventing and reducing middle ear fluid and equalizing middle ear pressure and for treatment of serous otitis media with effusion in infants and toddlers.

2. Description of the Prior Art

The Eustachian tube connects the back of the nose to the middle ear and allows air to enter the middle ear cavity behind the sealed eardrum. Contraction of the tensor veli palatini muscle is the most common way to open the Eustachian tube. This muscle contracts naturally through the act of swallowing. However, the muscle that opens the Eustachian tube in children is weaker than it is in adults. Furthermore, in an adult the Eustachian tube is rigid, approximately 3.5 to 3.9 cm in length and tilted downward by about 45 degrees. Whereas, the Eustachian tube in a child is less rigid, shorter in length and more horizontal in direction. Due to these differences between the Eustachian tubes of an adult and a child, fluid accumulated in the middle ear cavity of children is much less likely to be drained by the body though the Eustachian tube.

Serous otitis media with effusion, a common condition experienced by children, is an inflammation of the middle ear accompanied by a non-bacterial, thin, watery effusion. The main cause in children is that the Eustachian tube in children is weak and may not properly drain fluid from the middle ear. It may also be caused by inflammation of the middle ear mucosa resulting from, for example, a cold or an upper respiratory infection, blockage of or injury to the Eustachian tube, or a prior ear infection. Conservatively, 70 percent of all children will have at least one episode of middle ear effusion by the age of two. This inflammation of the middle ear mucosa may also prevent the Eustachian tube from opening normally.

When new oxygen is unable to enter the Eustachian tube, the middle ear mucosa will eventually absorb the remaining oxygen in the middle ear cavity, thus creating a vacuum and negative ear pressure, which may result in loss of hearing. Additionally, when the Eustachian tube does not open, clear fluid may eventually effuse from the mucosa of the middle ear and accumulate in the middle ear cavity, causing further hearing loss and possibly leading to further infection.

The middle ear includes the eardrum and three small bones behind the eardrum, i.e., the incus, malleus and stapes. The movement of these three bones transmits sound received by the eardrum, ultimately transmitting sound messages to the brain. Fluid in the middle ear cavity restricts movement of the eardrum and the three bones in the middle ear. Therefore, transmission of sound waves through the ear canal of children having fluid in their ears is diminished hearing.

Optimal functioning of the ear is attained when the air pressure in the middle ear cavity is equal to the ambient air pressure. When ambient air pressure is greater than or less than the air pressure in the middle ear, which may occur for example when in an airplane, pain and loss of hearing may occur. The Eustachian tube, by briefly opening, allows the body to adjust the air pressure in the middle ear so that it is equal to the ambient air pressure. This opening of the Eustachian tube is normally achieved through the act of swallowing, yawning or chewing. Eustachian tube dysfunction results when these actions do not open the Eustachian tube.

Since optimal functioning of the middle ear is attained when the air pressure in the middle ear cavity is equal to the ambient air pressure, treatment of middle ear fluid and Eustachian tube dysfunction requires a procedure for equalizing pressure and strengthening the Eustachian tube in children to accelerate the maturation of the muscle. Common treatments for serous otitis media with effusion are surgical implementation of pressure equalization tubes through the eardrum and/or the use of medication, such as steroids. The expense for such medical intervention is extremely high and makes it difficult for individuals in a lower socioeconomic position to afford such treatment. Moreover, these treatments have been shown to lack efficacy in many cases and treat merely the symptoms rather than the cause, which is the child's less effective Eustachian tube. Prevention and treatment avoiding surgery and medication are far more preferable for children, not to mention more affordable.

Current devices exist for equalizing pressure in the middle ear. For example, U.S. Pat. No. 5,885,242 describes a hand held apparatus having an air flow source for equalizing middle ear pressure. However, in order for the hand held apparatus to work, the user of the apparatus must swallow while activating the apparatus, supplying a continuous flow of air through the nostril and to the Eustachian tube. Synchronizing the acts of swallowing to open the Eustachian tube and providing a flow of air through the Eustachian tube while open is necessary to achieve equalization of middle ear pressure. Achieving synchronization of these two acts is more difficult with infants and toddlers.

A Politzer bag is routinely used in a physicians office for treating middle ear pressure and middle ear fluid. The physician places a tube in the patient's nostril and then squeezes the bag to create pressure within the nasal cavity. When the patient swallows, and pressure has built up, air will flow into the middle ear. The Politzer bag cannot, however, be used with infants and toddlers due to the high and imprecise pressure and volume flow resulting from squeezing the bag. In addition, there is again a lack of coordination between the flow of air from the bag and the act of swallowing, which need to occur almost simultaneously for the air to pass through the Eustachian tube.

In view of the foregoing, an apparatus and method for the prevention and treatment of middle ear fluid and Eustachian tube dysfunction in infants and toddlers, generally ranging in age from six months to two years of age, are provided to overcome the deficiencies in the prior art.

SUMMARY OF THE INVENTION

This and other objects of the invention are accomplished in accordance with the principles of the present invention by providing an apparatus and method for preventing and reducing middle ear fluid and equalizing middle ear pressure in infants and toddlers.

An apparatus having a flexible member connected to a main flexible tube and each adapted for insertion, respectively, in the mouth and in the nostril of a nose, is provided. The flexible member defines an air chamber for holding a specified amount of air. When the flexible member is placed in a child's mouth and compressed through the act of swallowing, air in the flexible member is forced to travel through the main flexible tube and into the nostril. Pores and valves, or sealing members, may be provided along the body of the main flexible tube so as to allow for unobstructed breathing before compression of the flexible member and to close off the pores and create an air conduit between the flexible member and the nostril when the flexible member is compressed. The air forced into the nostril at the time of swallowing traverses the Eustachian tube when in its open state (resulting from the act of swallowing), ultimately allowing the air to enter the middle ear cavity.

At the time the flexible member is compressed, the opposing nostril not receiving the air forced out of the flexible member must be occluded. The opposing nostril may be occluded by a supplemental flexible tube extending from the main flexible tube or through using any other applicable method or device of occlusion (e.g., a nose plug). Pores and valves may also be provided along the body of the supplemental tube to be inserted into the opposing nostril so as to allow for unobstructed breathing before compression of the flexible member and to prevent air external to the apparatus and air forced out of the flexible member when compressed from entering the opposing nostril.

The apparatus can be employed to prevent the occurrence of middle ear fluid in children by having the infant or toddler use it for a few minutes each day as an exercise to strengthen the Eustachian tube and accelerate the maturation of the tensor veli palatini muscle.

The apparatus can also be used as necessary to treat the occurrence of middle ear fluid or to relieve an imbalance between the air pressure within the middle ear and the external air pressure.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which.

DETAILED DESCRIPTION OF THE PREFERRED EMBODIMENTS

For purposes of clarity, and not by way of limitation, illustrative views of the present invention are described with references to FIGS. 1-6. The present invention is directed towards an apparatus and method for equalizing middle ear pressure. More specifically, the present invention relates to an apparatus and method for reducing middle ear fluid and equalizing middle ear pressure and for treatment of serous otitis media with effusion in infants and toddlers. The preferred embodiments of the present invention are illustrated, respectively, in FIGS. 1A and 1B.

Figure 1A:
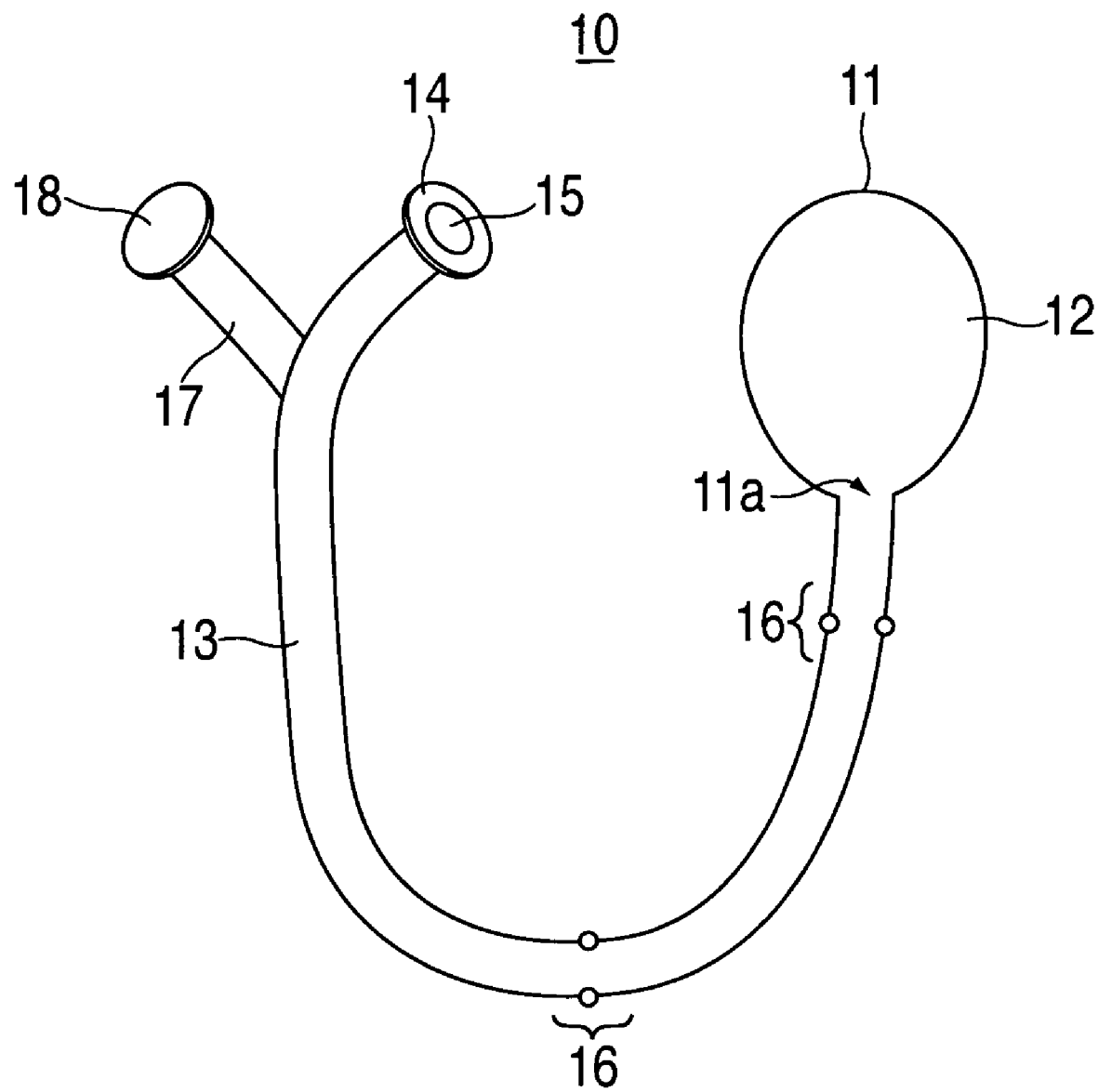
FIGS. 1A and 1B are illustrative views of an apparatus for treating middle ear fluid in accordance with the preferred embodiments of the present invention.

Apparatus 10 of FIG. 1A includes a flexible member 11 defining an air chamber 12, which may have various shapes, including a bulb. A main flexible tube 13 is connected to flexible member 11 at a chamber opening 11a of chamber 12. Pores and valves 16 may be integrated into the body of main flexible tube 13. Main flexible tube 13 may also have a nosepiece 14 with an opening 15 to permit air flow to exit at its end. Apparatus 10 may also include a supplemental flexible tube 17 having a closed nosepiece 18 at its end.

Figure 1B:
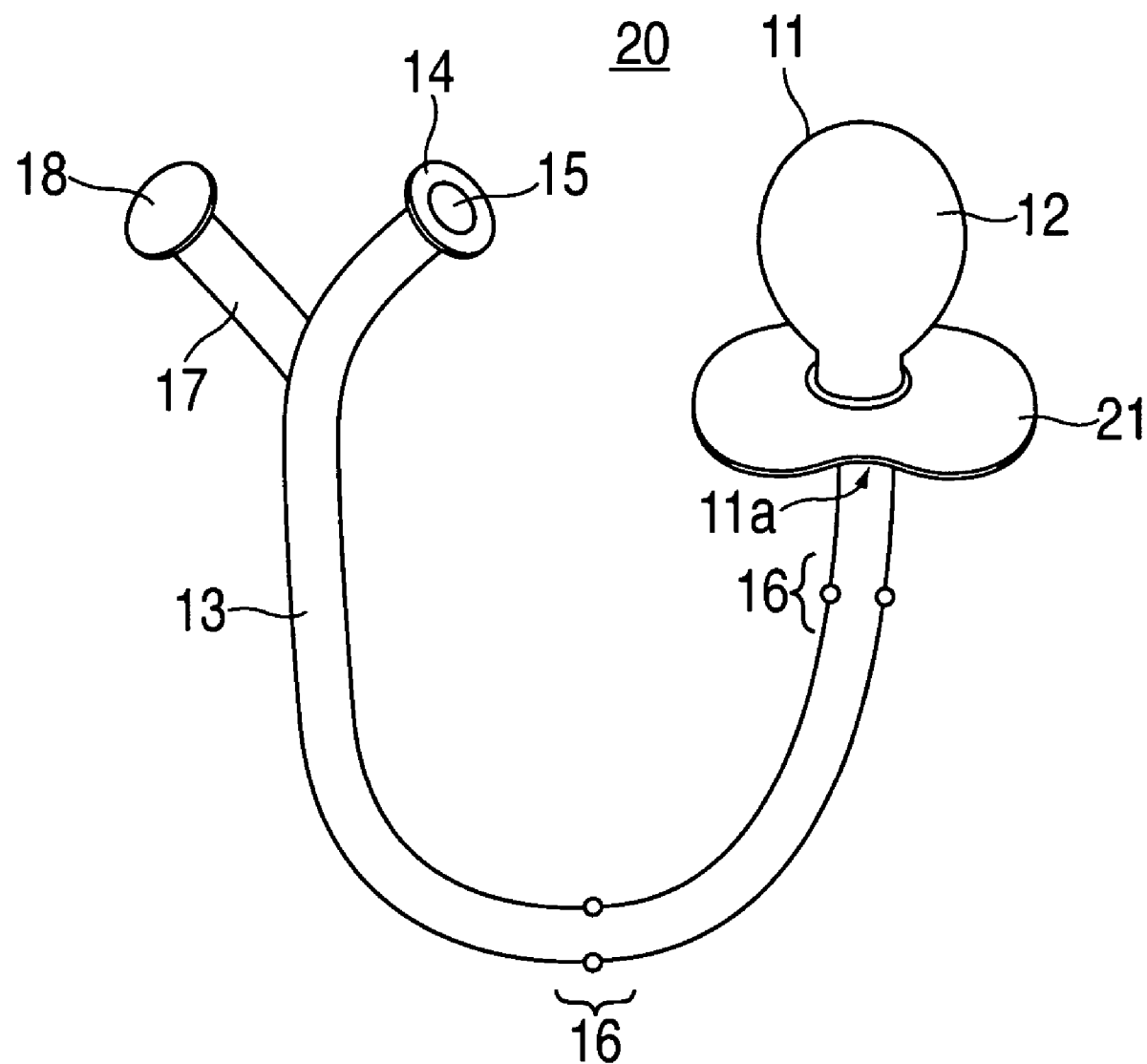

Apparatus 20 of FIG. 1B includes a mouth plate 21, which may be hard or flexible, connected to the end of flexible member 11 which may be shaped similar to a nipple, resembling an infant's pacifier. The purpose of this other preferred embodiment is to help induce an infant to receive flexible member 11 in his or her mouth. In addition, flexible member 11 may be dipped and coated with a sweet substance, such as honey, sugar water or milk, to further induce a child to accept flexible member 11 in his or her mouth.

Apparatus 20 has similar parts to apparatus 10 and is designed to operate in the same manner. Therefore the aforementioned descriptions are applicable to both embodiments. Flexible member 11 is constructed to be between 30-50 cubic centimeters in volume and is capable of providing approximately 200-600 daPa of pressure through main flexible tube 13 when flexible member 11 is compressed. Flexible member 11 is further constructed to be suitable for insertion into a mouth and is constructed with sufficient flexibility so that it may be compressed by the act of swallowing, as well as sufficient stiffness so that it is not compressed simply by insertion into the mouth. When flexible member 11 is compressed, air is forced out of chamber 12 through chamber opening 11a and forced to travel through main flexible tube 13 (described below in FIGS. 4 and 6).

Main flexible tube 13 with nosepiece 14 having an opening 15 may be adapted to be attached at the end of a first nostril. Nosepiece 14 may also be adapted for shallow insertion into the first nostril. Whether nosepiece 14 is adapted for attachment or shallow insertion into the first nostril, nosepiece 14 provides a seal from the external atmosphere. Nosepiece 14, for example, may be constructed of a soft, moldable hypoallergenic plastic that takes on the shape of the inside of a nostril to provide a seal from the external atmosphere. Alternatively, in another embodiment, main flexible tube member 13 may be adapted at one end without nosepiece 14 to be shallowly inserted in the first nostril and seal the first nostril from the external atmosphere. Upon sealing the first nostril, an air conduit is created between flexible member 11 and the nasal passageway extending from the first nostril.

Supplemental flexible tube 17 having nosepiece 18 at its end may be adapted for shallow insertion into a second nostril. When nosepiece 18 is inserted into the second nostril, the second nostril becomes sealed from the external atmosphere. Alternatively, supplemental flexible tube 17 may be adapted at one end without nosepiece 18 for shallow insertion into the second nostril to seal the second nostril from the external atmosphere. Supplemental flexible tube 17 may extend from any appropriate part of the body of main flexible tube 13. As illustrated in FIGS. 1A and 1B, supplemental flexible tube 17 is sealed off from main flexible tube 13 so as to prevent an air conduit from flexible member 11 through the body of supplemental flexible tube 17. Supplemental flexible tube 17, adapted with or without nosepiece 18, serves the purpose of occluding the second nostril, at least when flexible member 11 is compressed and air is forced through main flexible tube 13.

Apparatus 10 and apparatus 20 may also be constructed to exclude supplemental flexible tube 17. Alternatively, the second nostril may be occluded, thereby sealing the second nostril from the external atmosphere, by the use of a nose clip, a nose plug inserted into the second nostril, a finger pressed against the second nostril, or any other applicable device or method for occluding a nostril.

Apparatus 10 and apparatus 20 of FIGS. 1A and 1B, respectively, may be constructed by the combination of separate parts, such as, a flexible member part, a v-shaped flexible tube part (having main and supplemental flexible tubes), a main flexible tube absent a supplemental flexible tube part, and nosepiece parts. Apparatus 10 and apparatus 20 may also be constructed as a single unit, having proper combination of the aforementioned parts. The parts of apparatus 10 and apparatus 20 may be constructed from a soft, hypoallergenic plastic and may be disposable, either as a single unit or as individual disposable parts (e.g., nosepiece 14, flexible member 11, and/or flexible tubes 13 and 17).

Figure 2B:
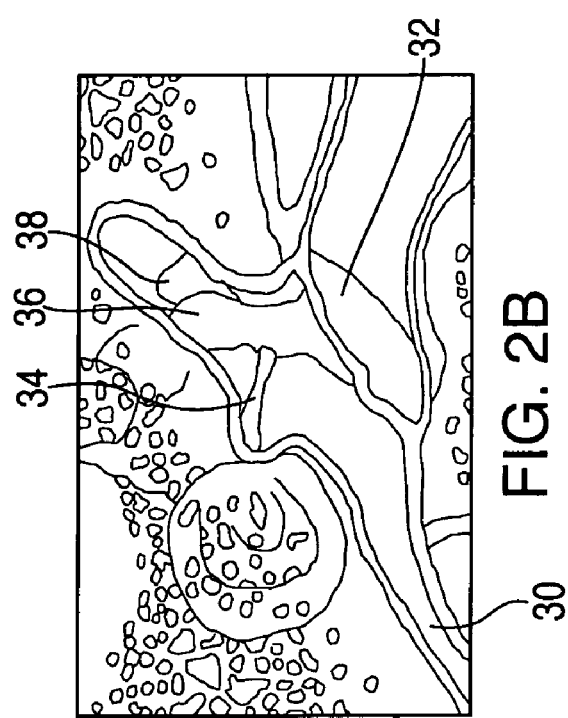
FIGS. 2B and 2C are enlarged illustrative views of the middle ear section illustrated in FIG. 2A in accordance with the preferred embodiments of the present invention.
Figure 2C:
Figure 2A:
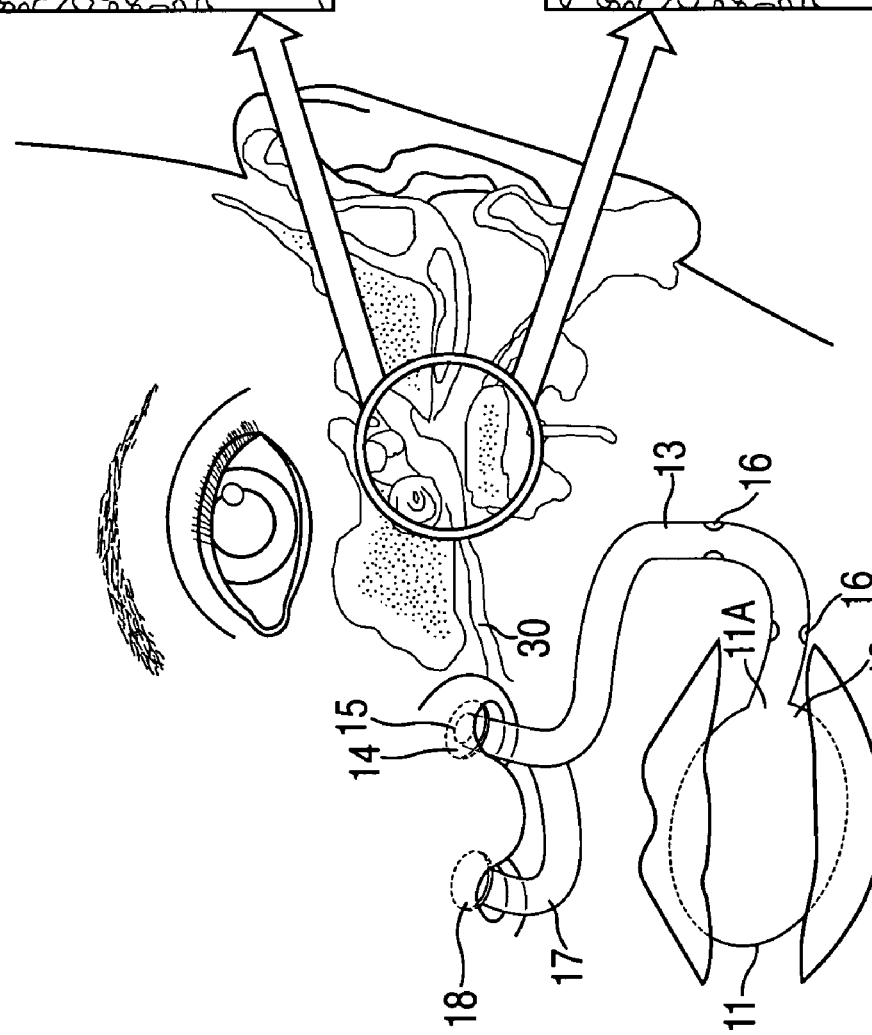
FIG. 2A is an illustrative view of the application of the apparatus illustrated in FIG. 1A in accordance with the preferred embodiments of the present invention.

FIGS. 2A-2C illustrate the application of apparatus 10 illustrated in FIG. 1A. FIGS. 2B and 2C, more specifically, provide an enlarged view, respectively, of the normal state of the middle ear and a state in which fluid has accumulated in the middle ear cavity. FIG. 2B illustrates the middle ear of a child absent middle ear fluid. The middle ear includes, as described earlier in the background of the invention, eardrum 32, the three bones, i.e., incus 38, malleus 36 and stapes 34, and Eustachian tube 30. FIG. 2C illustrates the middle ear of a child with fluid 40 in the middle ear cavity, which may significantly impact the proper functioning of incus 38, malleus 36, stapes 34 and eardrum 32 and ultimately result in hearing loss.

Apparatus 10 is used as shown in FIG. 2A to reduce middle ear fluid 40 illustrated in FIG. 2C. Apparatus 10 is made operational by inserting nosepiece 14 of main flexible tube 13 into a first nostril, occluding a second nostril (using supplemental flexible tube 17 or pressing closed the second nostril using a finger or some alternate means), inserting flexible member 11 into the mouth of the child and allowing the child to perform the act of swallowing so as to compress flexible member 11 and force pressurized air to travel through main flexible tube 13 and into the first nostril. The child can be induced to swallow by placing a few drops of milk in the child's mouth with the flexible member 11.

Apparatus 10 can be also be used as shown in FIG. 2A to prevent the occurrence of middle ear fluid 40 illustrated in FIG. 2C by strengthening the Eustachian tube and accelerating the maturation of the tensor veli palatini muscle. For this purpose, Apparatus 10 is made operational by having the infant or toddler use it for five to ten minutes, two to three times a week, even when there is no middle ear fluid 40 illustrated in FIG. 2C, employing the same method as described in FIG. 2A.

Figure 3:
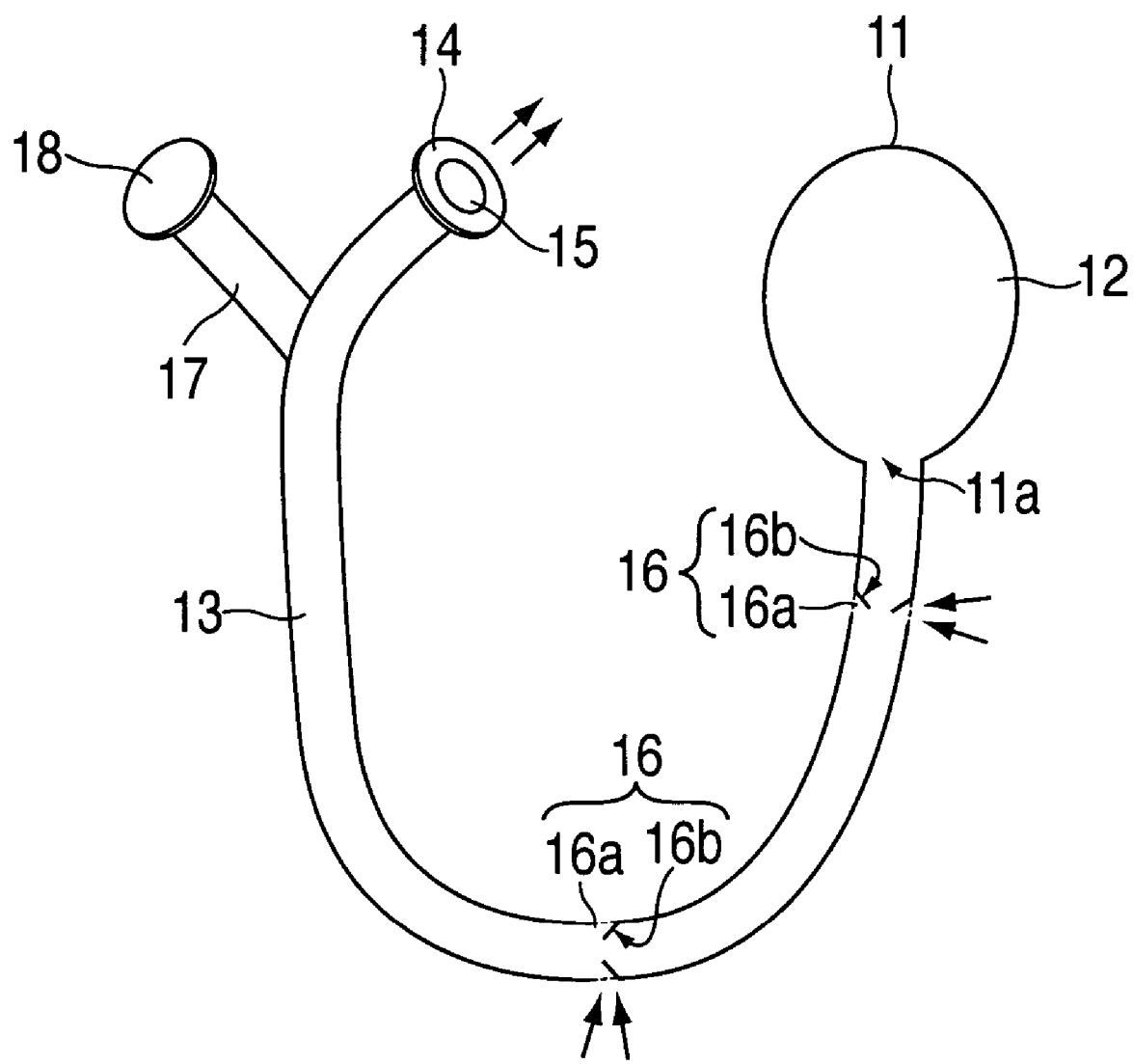
FIG. 3 is an illustrative view of the apparatus illustrated in FIG. 1A when the valves integrated along the main flexible tube are in their open position in accordance with the preferred embodiments of the present invention.

An enlarged view of pores and valves 16 in FIG. 1A are illustrated in FIG. 3, showing main flexible tube 13 having pores 16a and valves 16b integrated at points along the length of its body. Pores 16a are constructed so as to permit air from the outside atmosphere to flow freely in and out of main flexible tube 13. The flow of air permitted to travel through main flexible tube 13 allows for unobstructed breathing through the first nostril when main flexible tube 13 has been shallowly inserted into the first nostril. In addition, the flow of air into main flexible tube 13 allows for flexible member 11 to be inflated with air.

Figure 4:
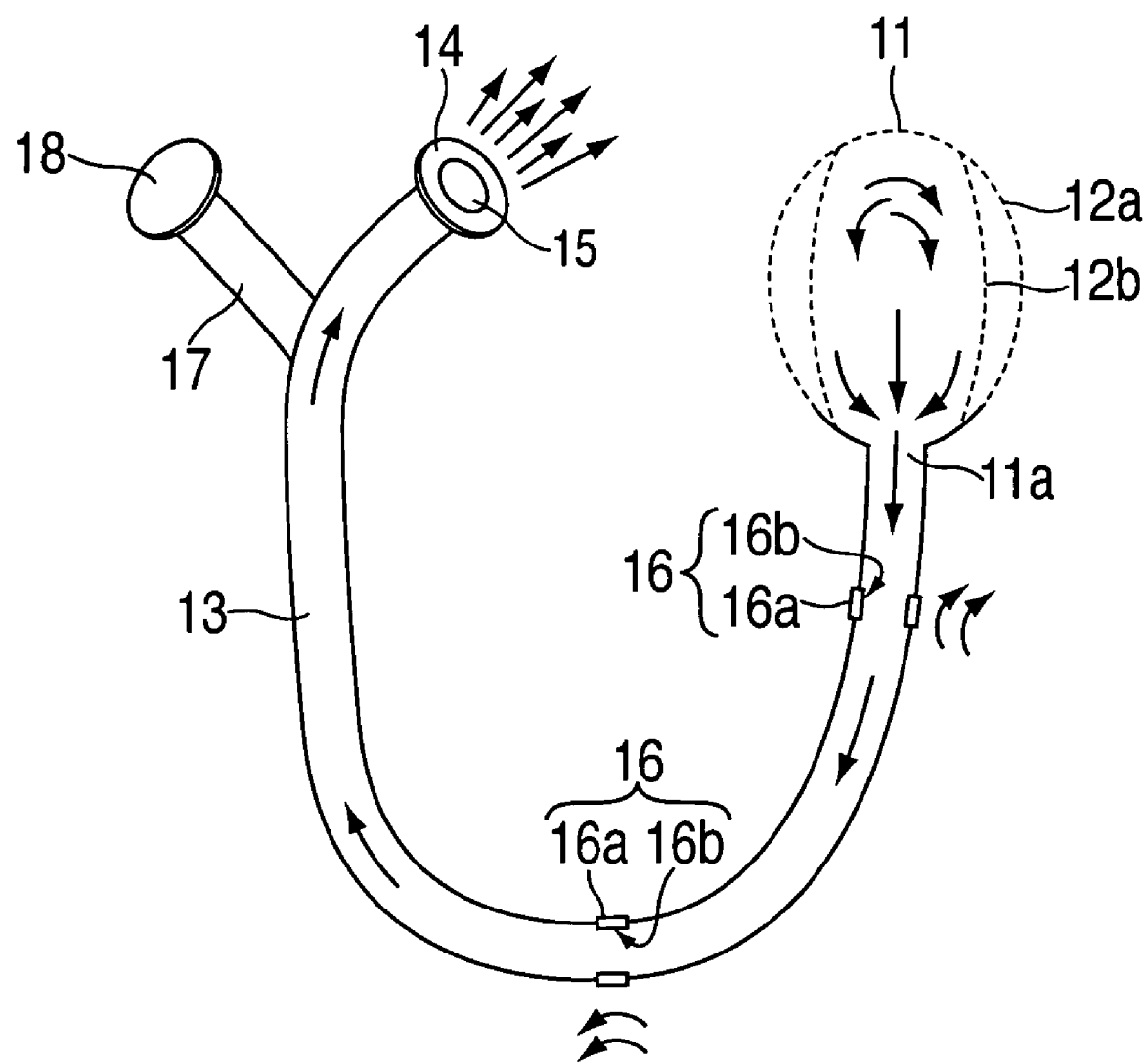
FIG. 4 is an illustrative view of the apparatus illustrated in FIG. 1A when the valves integrated along the main flexible tube are in their closed position in accordance with the preferred embodiments of the present invention.

Valves 16b of FIG. 3 are constructed so that when air is forced out of uncompressed air chamber 12a of FIG. 4, resulting in compressed air chamber 12b, through chamber opening 11a of flexible member 11 and into main flexible tube 13, the flow of air through main flexible tube 13 forces valves 16b, normally in an open state to allow air to flow in and out of main flexible tube 13, to close and prevent air from the outside atmosphere to enter through pores 16a, while preventing air being forced through main flexible tube 13 from exiting via pores 16a. Therefore an air conduit is formed between flexible member 11 and the nasal passageway of a nostril, as illustrated in FIG. 2A, permitting air forced through main flexible tube 13, upon swallowing and compressing flexible member 11, to enter the nasal passageway with the intended pressure. Compression of flexible member 11 forces the air contained in flexible member 11 through main flexible tube 13 and into the nasal passage of the first nostril leading to Eustachian tube 30 of FIGS. 2A and 2B. When flexible member 11 is compressed by the act of swallowing, Eustachian tube 30 is simultaneously opened by the act of swallowing, permitting air entering through the nasal passageway of the nostril to be forced through Eustachian tube 30 into the middle ear cavity. This simultaneous process equalizes middle ear pressure with that of the ambient pressure.

Figure 5:
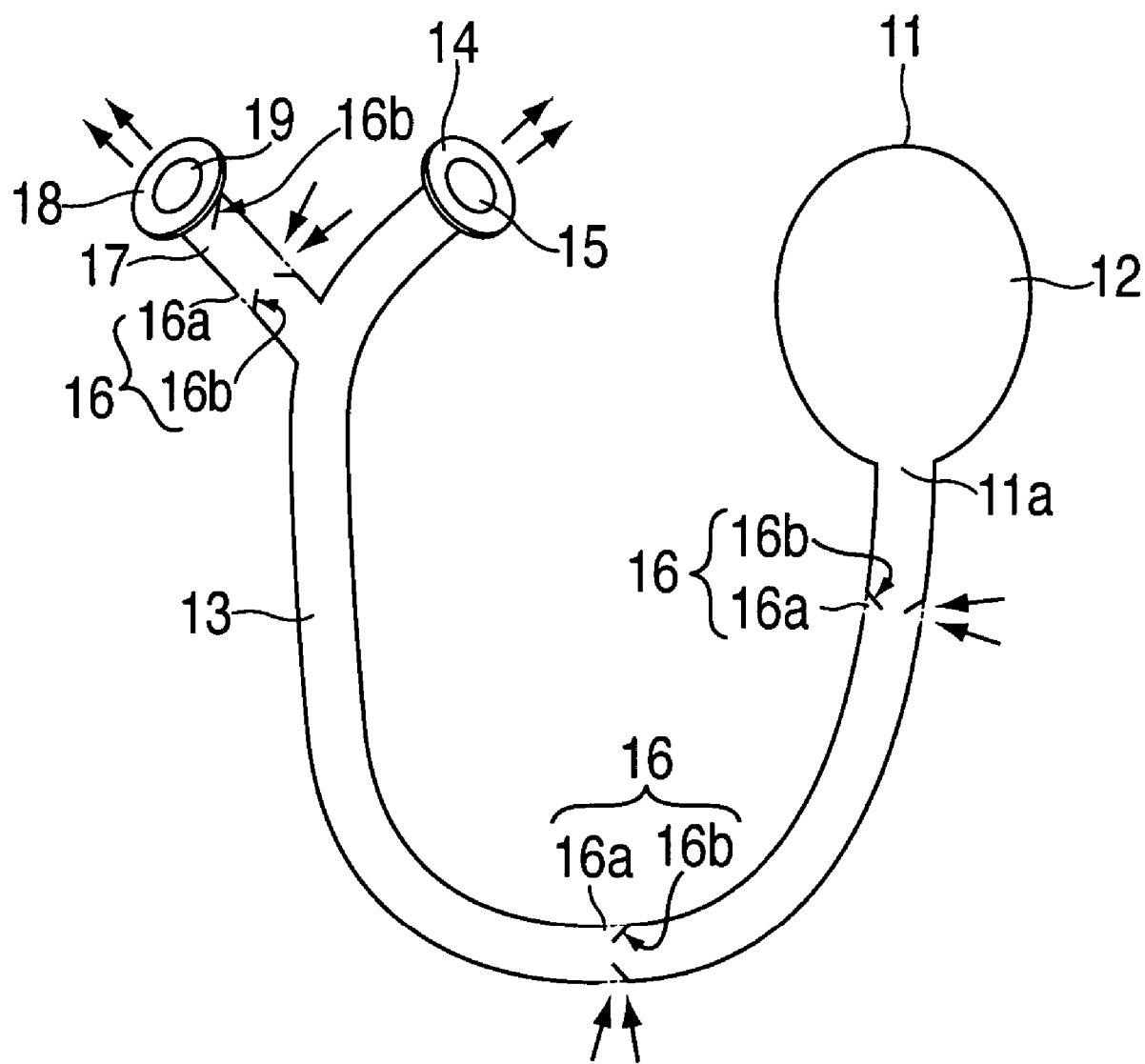
FIG. 5 is an illustrative view of an alternate embodiment of the apparatus illustrated in FIG. 1A having valves in their open position integrated along the body of the supplemental flexible tube.

An alternate embodiment of apparatus 10 of FIG. 1A is illustrated in FIG. 5. Here supplemental flexible tube 17 is constructed with pores 16a and valves 16b along its body. Supplemental flexible tube 17 is open to main flexible tube 13 or from flexible member 11. Therefore, air may enter supplemental flexible tube 17 from its pores 16a and from main flexible tube 13 or flexible member 11. The flow of air permitted to enter supplemental flexible tube 17 allows for unobstructed breathing through the second nostril by permitting air to flow through opening 19 of nosepiece 18 when supplemental flexible tube 17 has been shallowly inserted into the second nostril. Although supplemental flexible tube 17 ultimately serves the purpose of sealing the second nostril when air is forced into the first nostril by main flexible tube 13, unobstructed breathing is provided to both nostrils at the time main flexible tube 13 and supplemental flexible tube 17 are shallowly inserted into their respective nostrils and before flexible member 11 is compressed.

Figure 6:
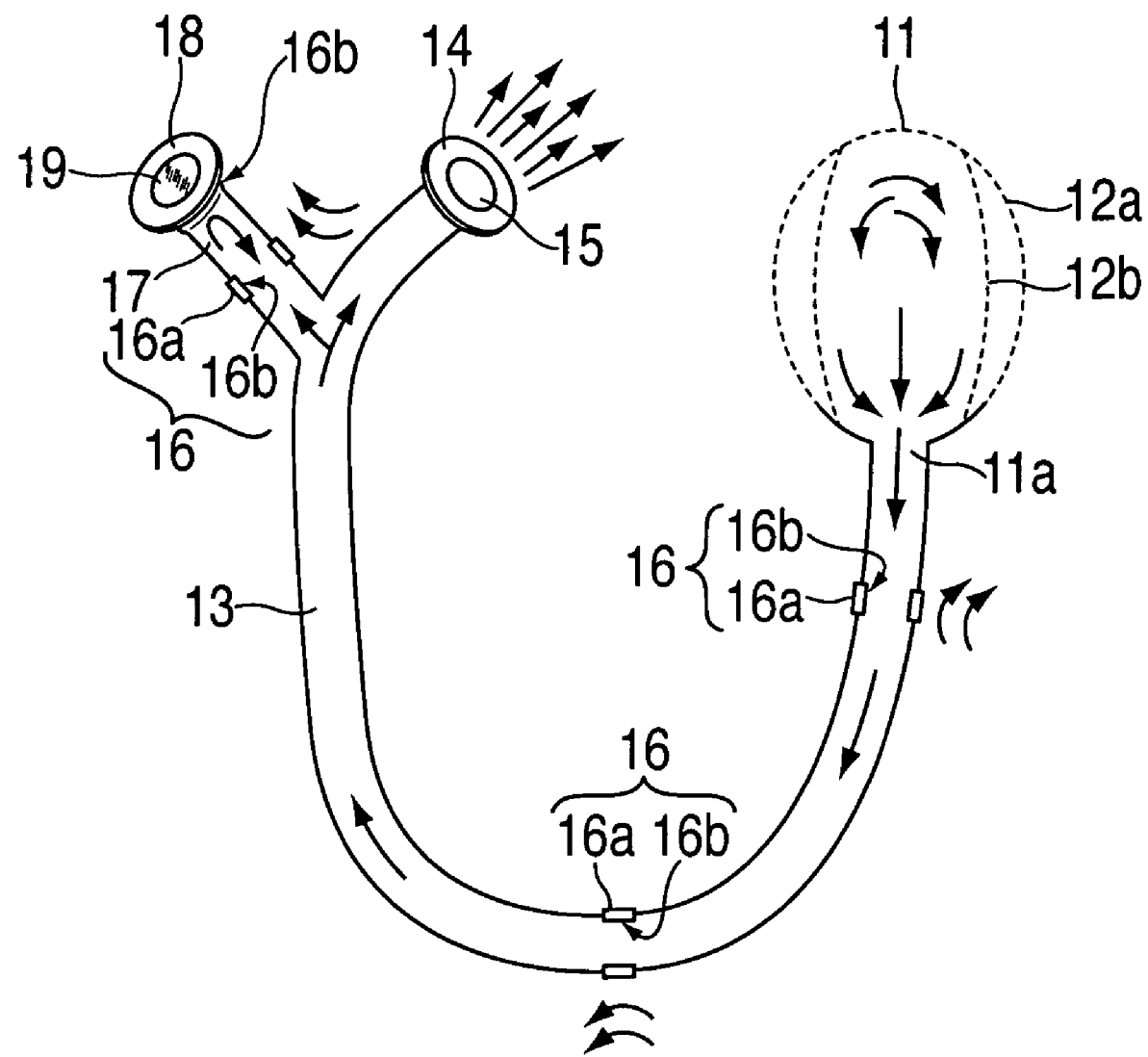
FIG. 6, is an illustrative view of an alternate embodiment of the apparatus illustrated in FIG. 1A having valves in their closed position integrated along the body of the supplemental flexible tube.

Since the second nostril must be occluded from the outside atmosphere at the time air is forced into the first nostril, valves 16b are also provided along the body of secondary flexible tube 17 to seal off pores 16a and opening 19. FIG. 6 illustrates the functionality of the alternate embodiment of apparatus 10. When air in uncompressed air chamber 12a of FIG. 6 is compressed by the act of swallowing, illustrated as compressed air chamber 12*b*, air is forced through chamber opening 11*a* of flexible member 11 and into main flexible tube 13 and supplemental flexible tube 17. The flow of air through main flexible tube 13 and secondary flexible tube 17 forces valves 16*b*, normally in an open state to allow air to flow freely in and out of main flexible tube 13 and secondary flexible tube 17, to close and prevent air from the outside atmosphere to enter through pores 16*a*, as well as prevent air being forced through main flexible tube 13 and secondary flexible tube 17 to exit through pores 16*a*. Therefore an air conduit is formed between flexible member 11 and the nasal passageway of the first nostril, permitting air forced through main flexible tube 13 to enter the nasal passageway of the first nostril with the intended air pressure to be forced through Eustachian tube 30 (FIG. 2A).

One skilled in the art will appreciate that the present invention can be practiced by other than the described embodiments, which are presented for purposes of illustration and not of limitation, and the present invention is limited only by the claims that follow.

We claim:

1. A method for reducing middle-ear fluid infants and toddlers, said method comprising:
   inserting a flexible member, defining an air chamber and having at least one opening, into a mouth;
   inserting into a first nostril a flexible tube which extends from said opening and creates an air conduit between said flexible member and said first nostril;
   occluding a second nostril; and
   compressing said flexible member by swallowing while occluding said second nostril, simultaneously opening the Eustachian tube and forcing air from said flexible member through said flexible tube into said nostril, allowing air from said flexible member to traverse the Eustachian tube into the middle ear.

2. The method defined in claim 1, wherein said second nostril is occluded by inserting a supplemental flexible tube constructed to occlude said second nostril at least when said flexible member is compressed.

3. The method defined in claim 1, wherein said second nostril is occluded by inserting a nose plug into said nostril.

4. The method defined in claim 1, wherein said second nostril is occluded by a clamp or a clip that presses against the outer edge of said second nostril to press it closed.

5. A method for preventing middle-ear fluid in infants and toddlers, said method comprising:
   inserting a flexible member, defining an air chamber and having at least one opening, into a mouth;
   inserting into a first nostril a flexible tube which extends from said opening and creates an air conduit between said flexible member and said first nostril;
   occluded a second nostril; and
   compressing said flexible member by swallowing while occluding said second nostril, simultaneously opening the Eustachian tube and forcing air from said flexible member through said flexible tube into said first nostril, allowing air from said flexible member to traverse the Eustachian tube into the middle ear.

* * * * *